United States Patent
Schillings et al.

(10) Patent No.: US 11,619,586 B2
(45) Date of Patent: Apr. 4, 2023

(54) SYSTEM FOR IMAGING AND SELECTIVE ILLUMINATION OF TARGETS WITHIN A SAMPLE

(71) Applicant: X Development LLC, Mountain View, CA (US)

(72) Inventors: Benoit Schillings, Los Altos Hills, CA (US); Anupama Thubagere Jagadeesh, San Jose, CA (US)

(73) Assignee: X Development LLC, Mountain View, CA (US)

( * ) Notice: Subject to any disclaimer, the term of this patent is extended or adjusted under 35 U.S.C. 154(b) by 0 days.

(21) Appl. No.: 17/370,184

(22) Filed: Jul. 8, 2021

(65) Prior Publication Data

US 2023/0010465 A1   Jan. 12, 2023

(51) Int. Cl.
| | | |
|---|---|---|
| *G01N 21/64* | (2006.01) | |
| *G02B 21/00* | (2006.01) | |
| *G02B 21/36* | (2006.01) | |
| *G02B 21/16* | (2006.01) | |
| *A61L 2/10* | (2006.01) | |

(52) U.S. Cl.
CPC ............ *G01N 21/6458* (2013.01); *A61L 2/10* (2013.01); *G01N 21/6428* (2013.01); *G02B 21/008* (2013.01); *G02B 21/0032* (2013.01); *G02B 21/16* (2013.01); *G02B 21/361* (2013.01); *A61L 2202/11* (2013.01); *A61L 2202/14* (2013.01);
(Continued)

(58) Field of Classification Search
CPC ....... G01N 21/6428; G01N 2021/6439; G01N 21/6458; G01N 2201/0675; A61L 2202/14; A61L 2/10; A61L 2202/11; G02B 21/0032; G02B 21/008; G02B 21/16; G02B 21/361
See application file for complete search history.

(56) References Cited

U.S. PATENT DOCUMENTS

| | | |
|---|---|---|
| 7,808,701 B2 | 10/2010 | Ouchi |
| 8,659,824 B2 | 2/2014 | Kato et al. |

(Continued)

OTHER PUBLICATIONS

Nichia Corporation NDU4116 Datasheet, 3 pages (Year: 2013).*

(Continued)

*Primary Examiner* — David P Porta
*Assistant Examiner* — Fani Polyzos Boosalis
(74) *Attorney, Agent, or Firm* — Fish & Richardson P.C.

(57) ABSTRACT

A system, including an optical imaging assembly configured to image a sample at an object plane to an image plane; an image sensor arranged at the image plane and configured to capture images of the sample for a field of view of the system; a light source configured to emit light having a wavelength, $\lambda$; a spatial light modulator (SLM) arranged to receive the light emitted from the light source and to provide a spatially modulated light pattern; one or more optical elements arranged to receive the spatially modulated light pattern from the SLM and to direct the spatially modulated light pattern to the image plane; and an electronic controller in communication with the image sensor and the spatial light modulator, the electronic controller being programmed to identify one or more targets in the field of view of the optical imaging assembly and to control the spatial light modulator to selectively direct light from the light source to the one or more targets identified by the electronic controller.

18 Claims, 5 Drawing Sheets

(52) U.S. Cl.
CPC ............... *G01N 2021/6439* (2013.01); *G01N 2201/0675* (2013.01)

(56) References Cited

U.S. PATENT DOCUMENTS

| | | | |
|---|---|---|---|
| 9,052,508 | B2 | 6/2015 | Yokoi |
| 9,069,167 | B2 | 6/2015 | Nishiwaki |
| 9,158,100 | B2 | 10/2015 | Yokoi |
| 9,239,456 | B2 | 1/2016 | Foelling |
| 9,535,242 | B1 | 1/2017 | Acosta |
| 10,698,225 | B2 | 6/2020 | Singer et al. |
| 10,908,403 | B2 | 2/2021 | Knop et al. |
| 2003/0021016 | A1* | 1/2003 | Grier ............... G02B 21/0036 359/368 |
| 2004/0089798 | A1* | 5/2004 | Gruber ............... G01N 15/1459 250/251 |
| 2007/0069119 | A1* | 3/2007 | Appleyard ............... G21K 1/00 359/641 |
| 2008/0316571 | A1 | 12/2008 | Macaulay |
| 2009/0296205 | A1 | 12/2009 | Ouchi |
| 2011/0109958 | A1 | 5/2011 | Yokoi |
| 2012/0206798 | A1 | 8/2012 | Knop et al. |
| 2013/0188250 | A1 | 7/2013 | Yokoi |
| 2013/0250391 | A1 | 9/2013 | Kato et al. |
| 2013/0271810 | A1 | 10/2013 | Yokoi |
| 2014/0061445 | A1 | 3/2014 | Foelling |
| 2014/0126048 | A1 | 5/2014 | Nishiwaki |
| 2015/0168732 | A1 | 6/2015 | Singer et al. |
| 2021/0131967 | A1 | 5/2021 | Studer |

OTHER PUBLICATIONS

Keeler et al., "The bactericidal effect of ultraviolet and visible light on *Escherichia coli*," Biotechnology and Bioengineering, Feb. 2008, 99(3):550-556.

* cited by examiner

SYSTEM FOR IMAGING AND SELECTIVE ILLUMINATION OF TARGETS WITHIN A SAMPLE

FIELD OF THE DISCLOSURE

The disclosure relates to a device and method for selectively illuminating targets within a sample (e.g., a biological sample) while imaging the sample.

BACKGROUND

Optical microscopes are extensively used in the study of microscopic samples, including biological samples. Further, light can be used to change the nature of certain samples. For instance, light at the appropriate wavelength and/or intensity can be used to kill living cellular organism. Ultraviolet light exposure, for example, can be used to kill bacteria.

SUMMARY

In general, the disclosure relates to identifying targets in a sample by analyzing microscope images of the sample and, using the same microscope system, selectively directing light onto one or more of the targets in the sample while the sample is in the field of view of the microscope.

In some examples, a user places a sample on an object plane of an imaging microscope system. An objective lens of the microscope images the sample onto an image sensor and the system processes captured images with an electronic controller to identify one or more targets within the sample images. To identify the targets within a sample, a user can provide one or more targeting parameters into the electronic controller. The electronic controller determines object spatial locations in the images that meet the targeting parameters and determines a corresponding spatial location at the object plane in the field of view of the microscope.

The microscope system also includes a light source and a spatial light modulator to direct light from the light source to the one or more targets in the field of view of the microscope based on the analyzed images. The light from the light source has a wavelength and/or intensity selected to interact with the targets in some specific way, e.g., to destroy or kill the targets. The SLM selectively exposes only the targets to the light, thereby avoiding adverse effects associated with exposing other regions of the sample to the light.

In some implementations, the sample and/or target can include biological organisms and the emitted light wavelength can deactivate the targets. In such examples, the microscope system operates to selectively deactivate a portion of the sample which meet the targeting parameters.

In general, in a first aspect, the invention features a system, including an optical imaging assembly configured to image a sample at an object plane to an image plane; an image sensor arranged at the image plane and configured to capture images of the sample for a field of view of the system; a light source configured to emit light having a wavelength, $\lambda$; a spatial light modulator (SLM) arranged to receive the light emitted from the light source and to provide a spatially modulated light pattern; one or more optical elements arranged to receive the spatially modulated light pattern from the SLM and to direct the spatially modulated light pattern to the image plane; and an electronic controller in communication with the image sensor and the spatial light modulator, the electronic controller being programmed to identify one or more targets in the field of view of the optical imaging assembly and to control the spatial light modulator to selectively direct light from the light source to the one or more targets identified by the electronic controller.

Embodiments may include one or more of the following features. The optical imaging assembly can be an optical microscope including an objective lens and a stage operable to position the sample at the objective plane. The image sensor can be a CCD sensor, or a CMOS sensor capable of imaging visible light. The wavelength can be in a range from 100 nm to 1400 nm. The wavelength can be in a range from 100 nm to 400 nm. The spatial light modulator can be a microelectromechanical systems (MEMS) mirror, a liquid crystal microdisplay, or one or more galvanometer optical scanners. The one or optical elements can image the spatial light modulator to the object plane. The one or more optical elements can include a beam expander. The one or more optical elements can include an objective lens separate from the optical imaging assembly (e.g., a confocal arrangement). The electronic controller can be programmed to identify a first population of biological organisms within a plurality of biological organisms as the one or more targets. The light source can be configured to emit light having a wavelength, $\lambda$, sufficient to deactivate the first population of biological organisms the electronic controller can be programmed to identify. The optical microscope can be a confocal microscope.

In a second aspect, the invention features a method, including capturing one or more images of a sample using an optical microscope; identifying, using an electronic processing system, one or more targets in the sample based on the one or more images; and while capturing the one or more images, selectively directing, using a spatial light modulator, light having a wavelength $\lambda$ to the one or more targets in the sample based on the identifying.

Embodiments may include one or more of the following features. The one or more targets can include one or more bacterial or eukaryotic cells. The one or more targets can include a fluorescent reporter molecule. The spatial light modulator can be a microelectromechanical systems (MEMS) mirror (e.g., a DLP, SLM, or adaptive mirror), a liquid crystal microdisplay, or one or more galvanometer optical scanners (e.g., capable of 2D scanning) The wavelength can be in a range from 100 nm to 1400 nm (e.g., UV to IR). The wavelength can be in a range from 100 nm to 400 nm (e.g., UV).

Among other advantages, the system includes a method to rapidly identify subpopulations of cellular biological samples and target them with directed light. Computer vision and machine learning algorithms can be trained to identify subpopulations based on various user-selected criteria increasing system flexibility for application in a number of situations.

Additionally, the components of the microscope system are conventional imaging and detection hardware in conjunction with conventional computer vision algorithms facilitating cost-effective image collection and target identification. The use of standard components also facilitates interchangeability of components and increases the system flexibility in various implementations.

Other advantages will be apparent from the description, the drawings, and the claims.

BRIEF DESCRIPTION OF THE DRAWINGS

In the figures, like symbols indicate like elements.

DETAILED DESCRIPTION

The disclosure describes a system for identifying targets including an optical imaging assembly, an electronic controller, and a spatial light modulator. The system identifies and deactivates targets within a sample by analyzing microscope images of the sample, identifying targets within the imaging system's field of view, and selectively directing light onto spatial locations within the field of view corresponding to the targets. The process selectively illuminates (e.g., in order to deactivate) the targets before changing the imaging field of view and identifying and illuminating additional targets.

Figure 1:
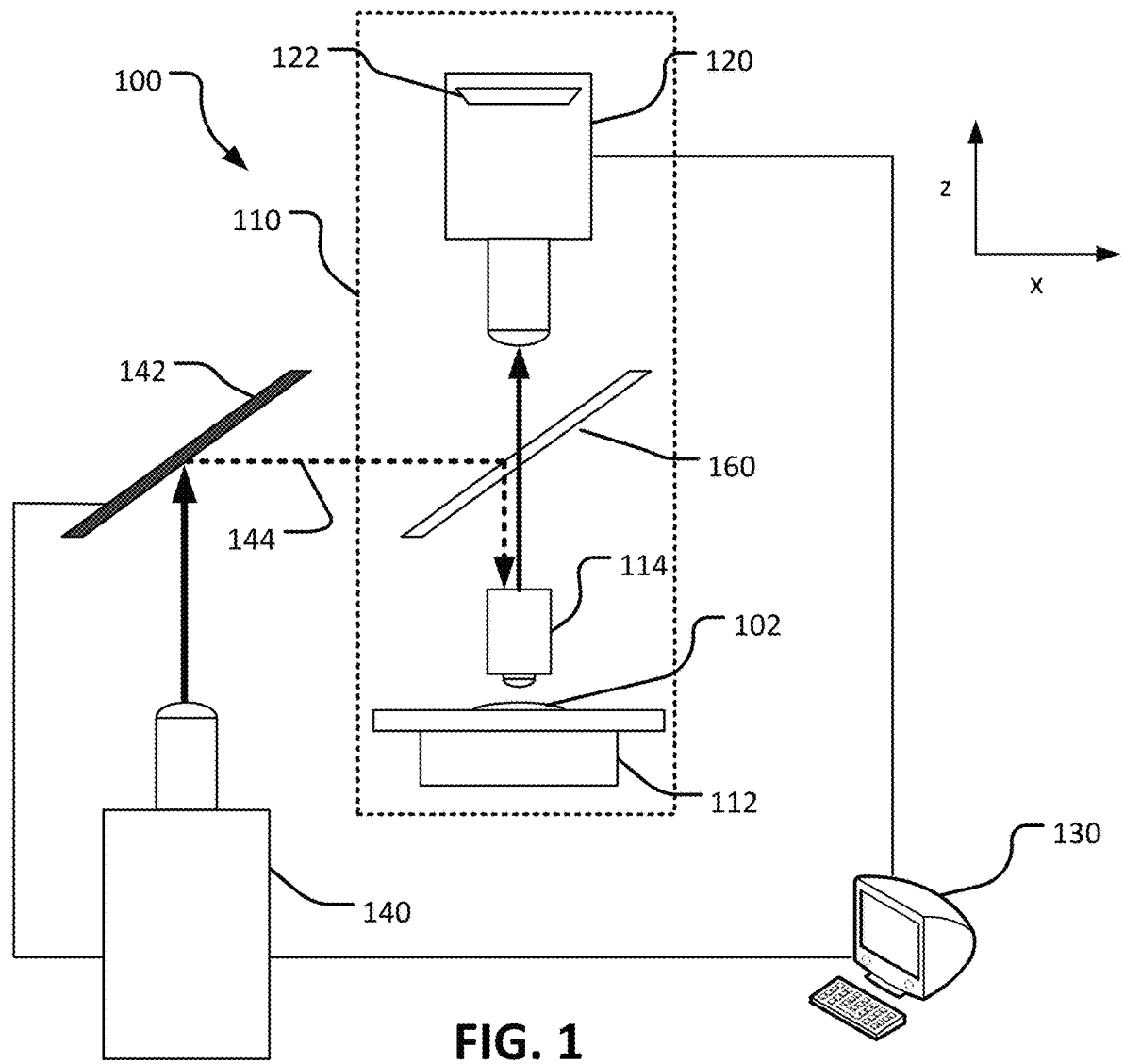
FIG. 1 is a schematic diagram of a selective illumination system.

FIG. 1 is a schematic diagram of a microscope system 100 configured to image an object plane containing a sample 102, identify one or more targets with the imaging field of view, and direct a spatially modulated light pattern to the sample 102 to deactivate (e.g., kill) the targets. In some implementations, the sample 102 is a biological sample including one or more biological organisms to be identified. Examples of biological organisms include eukaryotic or prokaryotic cells, such as cells from multi-cellular organisms (e.g., mammals, e.g., humans), yeasts, molds, viruses, bacteria, or archaea. The sample 102 can be a fresh or fixed tissue section, liquid suspension, or desiccated sample.

The microscope system 100 includes an optical imaging assembly 110 for imaging a field of view within a sample 102 object plane to an imaging device 120. The optical imaging assembly 110 includes a stage 112 operable to position the sample 102 along the x-, y-, and z-planes and an objective lens 114 which collects light from the object plane. A reference Cartesian coordinate system is shown in the top right of FIG. 1. In some implementations, the optical imaging assembly 110 is an optical microscope, such as a bright field, polarized, dark field, or phase contrast optical microscope. In some implementations, the optical imaging assembly 110 is a confocal optical microscope.

The optical imaging assembly 110 includes an illumination component which provides illumination light to the stage 112 and object plane. In some implementations, the illumination component is housed within the stage, beneath the stage, within the optical imaging assembly 110, or externally to the optical imaging assembly 110. Light emitted by the illumination component is delivered to the object plane via one or more optical elements, such as a mirror, lens, filter, or fiber optic cable. Examples of the illumination component include an incandescent bulb, a halogen bulb, an LED emitter, and/or a laser.

The illumination component provides illumination light to the stage 112 and the object plane and the sample, or objects within the sample, reflect, refract, or diffract the illumination light to the objective lens 114 which collects and transmits the light to the imaging device 120 which is arranged to collect the transmitted light and image the light to an image sensor 122 arranged at the image plane. In some implementations, the image sensor 122 is a CCD sensor, or a CMOS sensor capable of imaging light received from the object plane, such as light in the visible wavelength range, e.g., 380 nm to 700 nm. The image sensor 122 receives the light and converts the light to a digital image corresponding to the object plane field of view. The digital image is composed of an array of pixels, each pixel corresponding to light information collected at an x, y coordinate in the field of view.

The imaging device 120 includes components for wired or wireless electronic communication with an electronic controller 130, such as a serial bus port (e.g., USB), or wireless transducer (e.g., Bluetooth®, or Wi-Fi), and is in electronic communication with the electronic controller 130. The electronic controller 130 receives the digital image and causes a target identification program to process the digital image.

In some implementations, the target identification program is an image processing program including code to process a digital image and identify (e.g., recognize) the presence of one or more objects in the image field of view (e.g., targets). In some implementations, the image processing program is a computer vision algorithm capable of identifying object instances within a digital image. Generally, the algorithm identifies objects based upon example object classifications stored in and/or on electronic controller 130 memory or storage device. Each object classification includes one or more defining classification parameters which can include shape, size, aspect ratio, surface area, morphology (e.g., flagellum), presence of a marker (e.g., fluorescent reporter), count, optical density, spatial position, or pixel array position.

In some implementations, the object classifications and/or the object classification parameters can be created and/or updated (e.g., learned) based upon a machine learning algorithm, such as a convolutional neural network, stored in electronic controller 130 memory, and/or on a storage device, or in a networked location in electronic communication with the electronic controller 130.

One or more object classifications can include a target flag identifying the object classification as a target. In some implementations, the object classifications which include target flags are determined by user input to the electronic controller 130, or by targeting parameters stored in the electronic controller 130 memory and/or storage device. Targeting parameters can include one or more parameters defining an object classification, as described above.

The image processing program identifies one or more objects within the digital image and determines an object classification and a spatial position corresponding to each identified object. In some implementations, the determining includes identifying spatial orientation markers (e.g., fiducial markers), such as any markers present on the stage 112, in the sample 102, or on the sample 102 slide. Fiducial markers can represent a fixed spatial position corresponding to x, y coordinates in the optical imaging assembly 110 object plane field of view. One or more fiducial markers appearing on digital images imaged by the imaging device 120 decrease identified object spatial position error. The image processing program compiles the spatial position and associated error of each target into a targeting data structure.

The light source 140 emits light having a wavelength, λ. Examples of light source 140 include an incandescent bulb, a halogen bulb (e.g., tungsten-halogen, or xenon), an LED emitter, or a laser. In some implementations, the light source 140 emits light in a wavelength range from 100 nm to 1400 nm (e.g., UV to IR). Light emitted by the light source 140 can be modified by one or more optical elements before being imaged to the object plane. For example, one or more optical elements can be used to modify the spectral content, intensity, and/or beam shape of the light from light source 140. An optical filter, for example, can be used to modify the spectral content of the light, e.g., to produce narrowband illumination (e.g., a wavelength spectrum full-width half-max (FWHM) of less than 10 nm) from a broadband source. Optical elements such as lenses, mirrors, and/or gratings can be used to shape the beam from light source 140. An aperture stop (e.g., a diaphragm) can be used to stop the beam down.

Some examples of light source 140 includes lasers emitting approximately monochromatic light (e.g., a wavelength spectrum FWHM of 5 nm or less), or an LED emitting a narrowband emission of light (e.g., a wavelength spectrum FWHM of 50 nm or less), at a wavelength capable of disrupting biological organisms through one or more means. For example, UV light is effective at deactivating biological organisms through disruption of membranes and nucleic acids and in some implementations, the light source 140 emits light in a wavelength range from 100 nm to 400 nm (e.g., 200 nm to 280 nm). For example, UV light at either 254 nm or 222 nm is known to disrupt the base pair interactions in double-stranded nucleotides in microorganisms, overwhelming the DNA repair machinery and causing cellular inactivation. Without wishing to be bound by theory, a UV light dose in a range between 2,000 and 80,000 $\mu W \cdot s/cm^2$ inactivates the majority of many microbial organisms present (e.g., >90%, or >99%).

For example, Rotaviruses are deactivated (e.g., at least a log 3 reduction in inactivated microbial organisms, >99.9%) at a dose of 32 mW s/cm$^2$, Hepatitis B are deactivated at a dose of 25 mW s/cm$^2$, *Salmonella Typhimurium* are deactivated at a dose of 22 mW s/cm$^2$, *Staphylococcus aureus* are deactivated at a dose of 3.2 mW s/cm$^2$, and *Streptococcus faecalis* are deactivated at a dose of 9.8 mW s/cm$^2$.

A spatial light modulator 142 (SLM) is arranged to receive light emitted from the light source 140 and is in electronic communication with the electronic controller 130. The electronic controller 130 provides the targeting data structure to the spatial light modulator 142 which processes the targeting data structure and determines a correction to the light received from the light source 140. In alternative implementations, the electronic controller 130 determines the correction based on the targeting data structure(s) and provides the correction to the spatial light modulator 142.

The spatial light modulator 142 applies the correction by imposing a spatially varying modulation to the received light and creates a spatially modulated light pattern 144. In some implementations, the spatial light modulator 142 is a microelectromechanical systems (MEMS) mirror (e.g., a DLP, SLM, or adaptive mirror), a liquid crystal microdisplay, or one or more galvanometer optical scanners (e.g., capable of 2D scanning).

The light pattern 144 includes one or more targeted light features (e.g., spots) into which the spatial light modulator 142 concentrates at least a portion of the received light intensity. The light features are arranged within the light pattern 144 corresponding to the target spatial location(s) within the targeting data structure. In some implementations, the light features can be characterized by a spot size and a peak intensity. Spot size can be determined as the FWHM for example.

The light feature (e.g., FWHM) at the object plane can correspond to or be based on the optics used to direct light from the spatial light modulator to the object plane. The light feature size can be in a range from 1 nm to $10^6$ nm. The spot size can correspond to the target to be deactivated and in some cases can be included in the targeting structure. For example, a eukaryotic cell target having a size of 20 µm, or a bacterial target having a size of 5 µm, can correspond to a similar spot size. In cases in which the spatial resolution of the spatial light modulator 142 is greater than the target spatial size (e.g., viruses), the spatial light modulator 142 delivers a light pattern 144 including light features having high intensities (e.g., high peak intensity) such that a minimum dose is delivered to the target cross section. For example, the light features can have an intensity 100 µW/cm$^2$ or more.

In some implementations, the light source 140 can be a pulsed light source. Pulse duration can be in a range from $10^{-9}$ s to 1 s or longer during which a particular light pattern 144 is delivered to the object plane.

In some implementations, the targeting structure includes a dose threshold corresponding to the identified object. For example, a bacterial targeting structure includes a dose threshold of 8,000 µW/cm$^2$, and a mold targeting structure includes a dose threshold of 20,000 µW/cm$^2$. The electronic controller 130 controls the light source 140 and the spatial light modulator 142 to deliver the light pattern 144 including light features having an intensity and duration above the dose threshold. For example, a light feature having a peak intensity of 1000 µW/cm$^2$ and a duration of 0.1 s delivers a dose of 100 µW·s/cm$^2$. The dose threshold can depend on the target type, light feature spatial resolution, light pattern 144 wavelength, and can be in a range from 100 µW·s/cm$^2$ to 100,000 µW·s/cm$^2$.

The spatial light modulator 142 directs the spatially modulated light pattern 144 to the object plane within the sample 102. The light pattern 144 features correspond to target spatial positions within the field of view such that each target receives a portion of the light pattern 144 total intensity. The light pattern 144 can include one or more light feature and in some implementations, the light feature is non-circular. In some implementations, the light feature geometry at the object plane conforms to or corresponds with the target cross-sectional shape (e.g., oblong, circular, or asymmetric). In some implementations, the light pattern 144 includes a light feature for each target determined to be in the optical imaging assembly 110 field of view.

In some implementations, the system 100 includes one or more optical elements 160 in the spatially modulated light pattern 144 travel path to image the pattern to the object plane. In various example implementations, the one or more optical elements 160 includes a beam expander, half mirror, prism, or beamsplitter.

Figure 2:
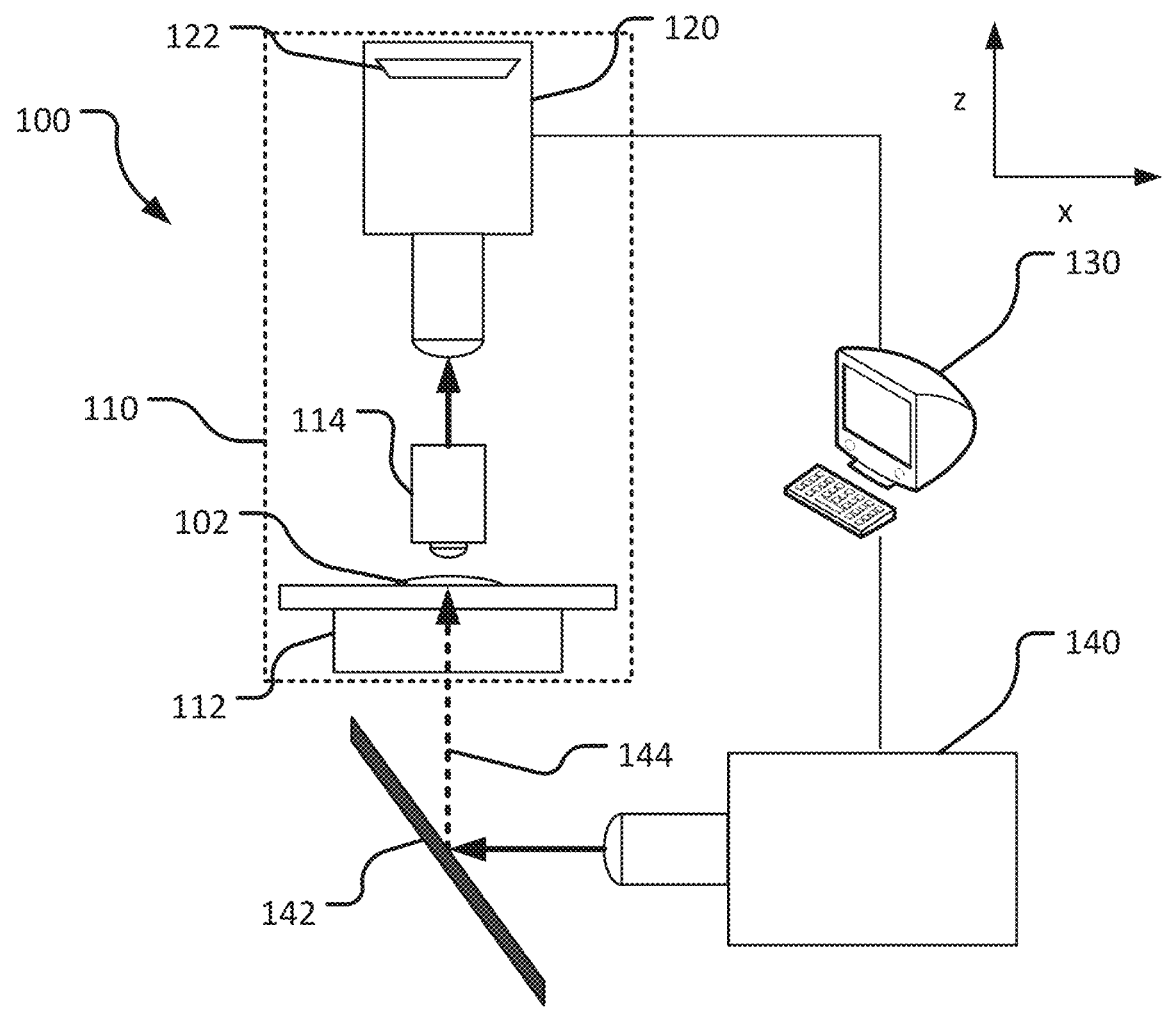
FIG. 2 is a schematic diagram of a second arrangement of the selective illumination system.

FIG. 2 is a schematic diagram of an alternative arrangement of the microscope system 100 in which the spatially modulated light pattern 144 of the light source 140 and spatial light modulator 42 are imaged to the object plane field of view in the sample 102 from beneath the stage 112. Such implementations may not include optical elements 160 for imaging the light pattern 144.

Figure 3A:
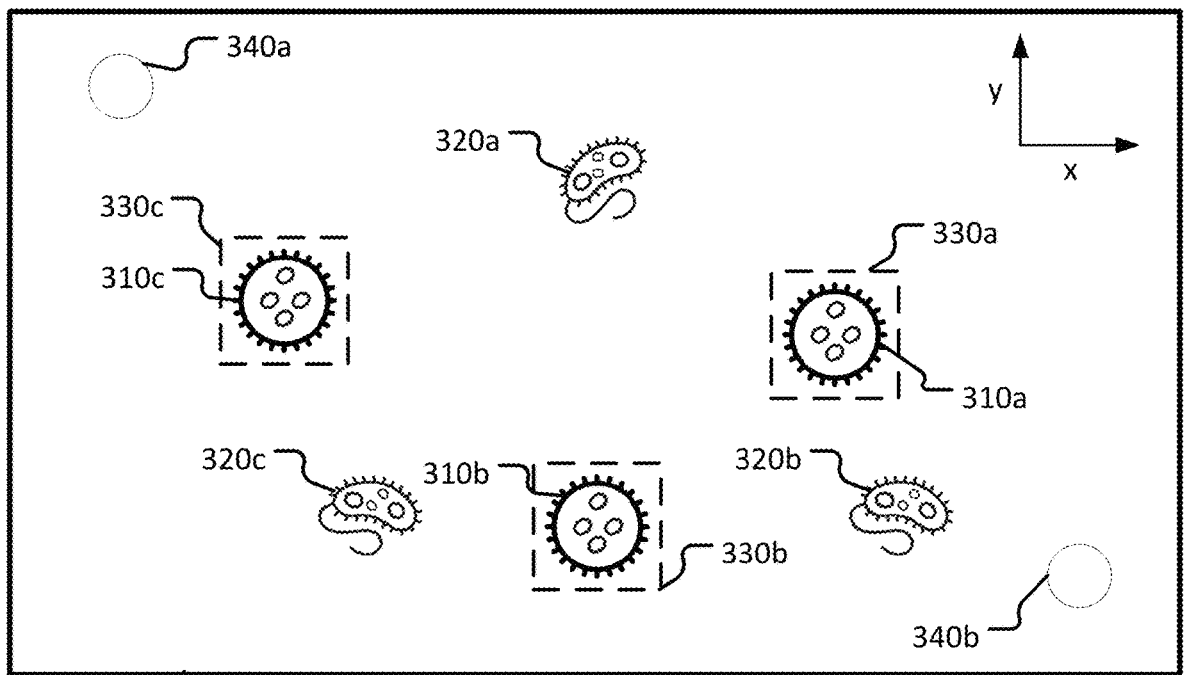
FIG. 3A is a schematic diagram of an imaging field of view including multiple object types.

Referring now to FIG. 3A, an example field of view 300 is shown as imaged by the image sensor 122 and received by the electronic controller 130 for processing. The field of view 300 contains a portion of the object plane corresponding to a spatial region within the sample 102. The field of view 300 spatial region is determined based on the total magnification of the optical imaging assembly 110, such as the combined magnification of the objective lens 114 and/or imaging device 120.

The field of view 300 spatial region includes bounding dimensions (e.g., such as the field of view 300 height and width of FIG. 3A, or a diameter of a circular field of view 300) which define a spatial region area. The bounding dimensions can be in a range from 1 µm to $10^4$ µm. In alternative implementations, the spatial region area is in a range from $2.5 \times 10^2$ µm$^2$ to $10^8$ µm.

The field of view 300 contains three object populations including a first microbe population 310 (e.g., microbes 310*a*, 310*b*, and 310*c*), a second microbe population 320 (e.g., microbes 320*a*, 320*b*, and 320*c*), and fiducial markers 340 (e.g., fiducial markers 340*a* and 340*b*). The fiducial markers 340 facilitate the field of view 300 spatial orientation during electronic controller 130 processing.

In the example field of view 300, the electronic controller 130 identifies the first microbe population 310, second microbe population 320, and fiducial markers 340 based on at least one classification parameter stored in memory and/or storage. The electronic controller 130 determines the spatial position of the first microbe population 310 based on at least the field of view 300 spatial orientation with respect to the sample 102 and stage 112.

The electronic controller 130 targets a population of classified objects, denoted by the targeting boundaries 330, e.g., targeting boundaries 330*a*, 330*b*, and 330*c* containing microbes 310*a*, 310*b*, and 310*c*, respectively. In the example of FIG. 3, electronic controller 130 targets first microbe population 310 by creating a targeting data structure including the spatial position of each microbe of first microbe population 310 (e.g., microbes 310*a*, 310*b*, and 310*c*). In some implementations, the electronic controller 130 creates additional targeting data structures for additional populations of classified objects.

Figure 3B:
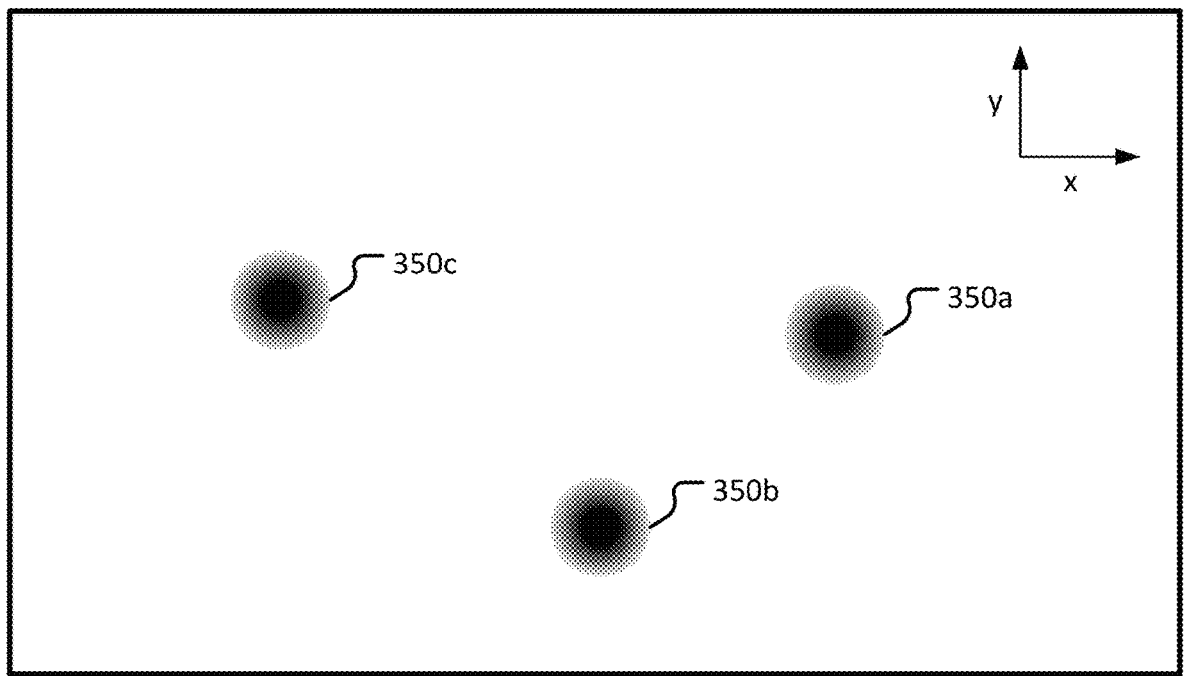
FIG. 3B is a schematic diagram of a light pattern including multiple light features.

The electronic controller 130 then controls the light source 140 and spatial light modulator 142 to create a light pattern 144 including light features corresponding with the targeted objects. The light pattern 144 is directed to the sample 102 object plane by the optical elements 160. FIG. 3B depicts the light pattern 144 including radially-symmetric light features 350*a*, 350*b*, and 350*c* (collectively light features 350) as delivered to the sample 102 object plane. The light features 350 spatial locations correspond with the targeting boundaries 330 within the field of view 300 of FIG. 3A.

Figure 4:
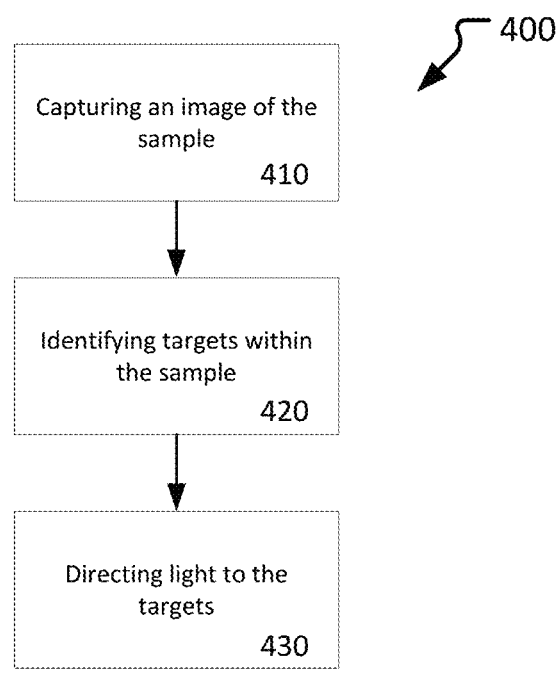
FIG. 4 is a flow chart diagram of a method of directing light to a set of identified targets in a sample.

FIG. 4 is a flow chart diagram depicting the target identification process 400 within a sample. The microscope system 100 includes an optical imaging assembly 110 which captures one or more digital images of an object plane field of view within a sample 102 (step 410). An electronic controller 130 in electronic communication with the optical imaging assembly 110 receives the digital images and processes the digital images using one or more algorithms stored in memory or on a storage device. In some implementations, the one or more algorithms can include a machine learning or computer vision algorithm.

The electronic controller 130 identifies, using the one or more algorithms, a target within the digital image of the object plane based on an object classification (step 420). Each object classification stored on the electronic controller 130 includes one or more object classifications parameters which defines the object classification. The electronic controller 130 determines object parameters for each identified object and compares the identified object parameters to object classifications parameters to determine an object classification for each identified object. If an identified object classification includes a targeting flag, the electronic controller 130 identifies the object as a target.

The electronic controller 130 determines the spatial position of each target within the field of view 300. In some implementations, the electronic controller 130 determines the spatial position of one or more fiducial markers 340 within the field of view 300 and uses the fiducial markers 340 spatial positions to determine the target spatial position. The electronic controller 130 provides the target spatial positions to the spatial light modulator 142 which determines a correction. In some implementations, the electronic controller 130 determines the correction based on the targeting data structure(s) and provides the correction to the spatial light modulator 142.

The spatial light modulator 142 receives light from the light source 140 and applies the correction to the received light creating a spatially modulated light pattern 144. The light pattern 144 is directed to the object plane and includes a wave front having peak intensities corresponding to the spatial position of each identified target within the object plane (e.g., in sample 102) (step 430). The light can have a wavelength sufficient to deactivate the target, or a component within the target, such as a UV (e.g., in a range from 100 nm to 400 nm) or IR (e.g., in a range from 800 nm to 1400 nm).

The microscope system 100 performs steps 410, 420, and 420, of the target identification process 400 continuously, or sequentially, for each field of view 300 in the object plane.

Figure 5:
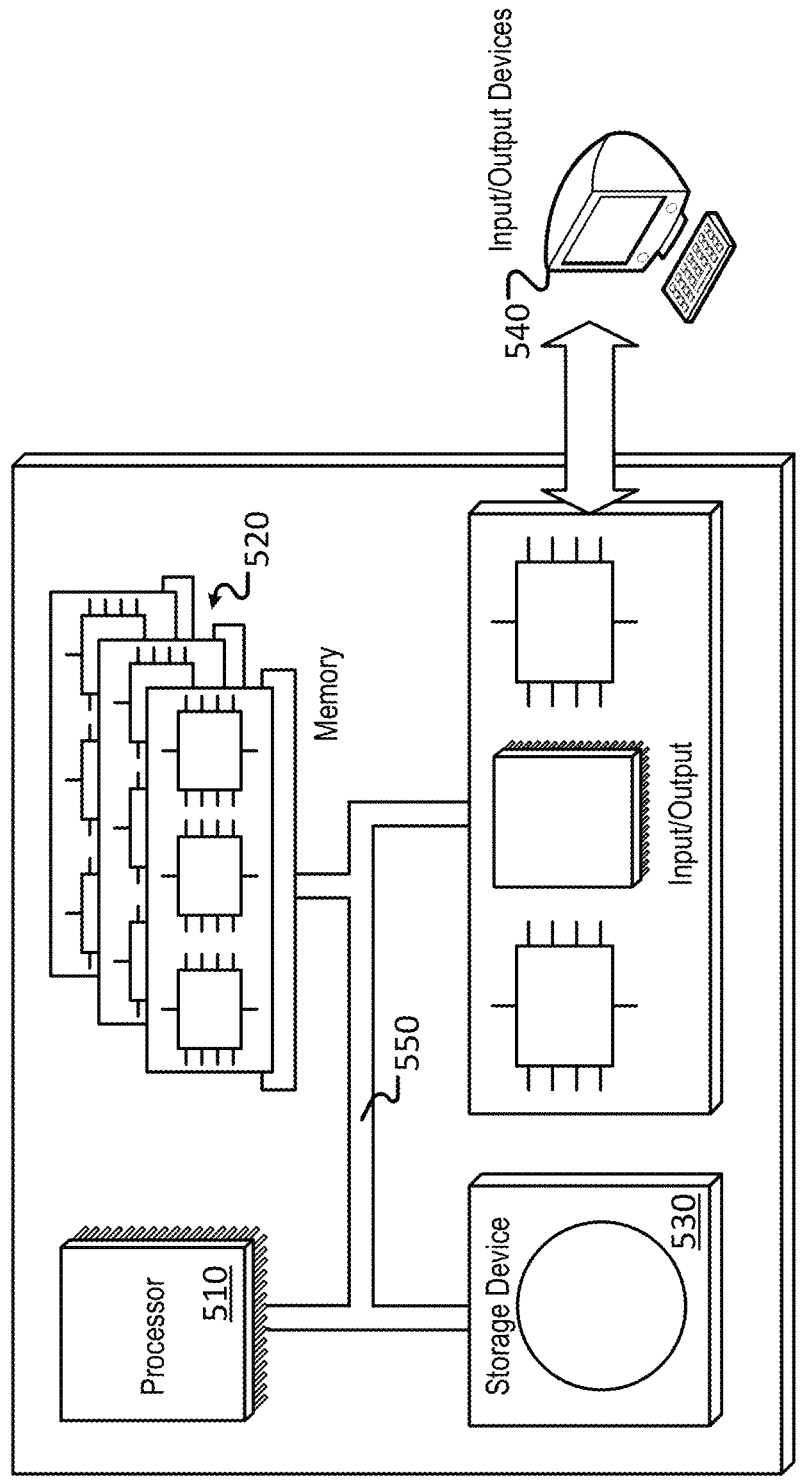
FIG. 5 is a schematic diagram of an example electronic controller.

FIG. 5 is a schematic diagram of an exemplary electronic controller 500. The electronic controller 500 can be used to carry out the operations described in association with any of the computer-implemented methods described previously, according to some implementations. In some implementations, computing systems and devices and the functional operations described in this specification can be implemented in digital electronic circuitry, in tangibly-embodied computer software or firmware, in computer hardware, including the structures disclosed in this specification (e.g., electronic controller 500) and their structural equivalents, or in combinations of one or more of them. The electronic controller 500 is intended to include various forms of digital computers, such as laptops, desktops, workstations, personal digital assistants, servers, blade servers, mainframes, and other appropriate computers, including vehicles installed on base units or pod units of modular vehicles. The electronic controller 500 can also include mobile devices, such as personal digital assistants, cellular telephones, smartphones, and other similar computing devices. Additionally, the system can include portable storage media, such as, Universal Serial Bus (USB) flash drives. For example, the USB flash drives may store operating systems and other applications. The USB flash drives can include input/output components, such as a wireless transducer or USB connector that may be inserted into a USB port of another computing device.

The electronic controller 500 includes a processor 510, a memory 520, a storage device 530, and an input/output device 540. Each of the components 510, 520, 530, and 540 are interconnected using a system bus 550. The processor 510 is capable of processing instructions for execution within the electronic controller 500. The processor may be designed using any of a number of architectures. For example, the processor 510 may be a CISC (Complex Instruction Set Computers) processor, a RISC (Reduced Instruction Set Computer) processor, or a MISC (Minimal Instruction Set Computer) processor.

In one implementation, the processor 510 is a single-threaded processor. In another implementation, the processor 510 is a multi-threaded processor. The processor 510 is capable of processing instructions stored in the memory 520 or on the storage device 530 to display graphical information for a user interface on the input/output device 540.

The memory 520 stores information within the electronic controller 500. In one implementation, the memory 520 is a computer-readable medium. In one implementation, the memory 520 is a volatile memory unit. In another implementation, the memory 520 is a non-volatile memory unit.

The storage device 530 is capable of providing mass storage for the electronic controller 500. In one implementation, the storage device 530 is a computer-readable medium. In various different implementations, the storage device 530 may be a floppy disk device, a hard disk device, an optical disk device, or a tape device.

The input/output device 540 provides input/output operations for the electronic controller 500. In one implementation, the input/output device 540 includes a keyboard and/or pointing device. In another implementation, the input/output device 540 includes a display unit for displaying graphical user interfaces.

The features described can be implemented in digital electronic circuitry, or in computer hardware, firmware, software, or in combinations of them. The apparatus can be implemented in a computer program product tangibly embodied in an information carrier, e.g., in a machine-readable storage device for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer. Additionally, such activities can be implemented via touch-screen flat-panel displays and other appropriate mechanisms.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include a local area network ("LAN"), a wide area network ("WAN"), peer-to-peer networks (having ad-hoc or static members), grid computing infrastructures, and the Internet.

The computer system can include clients and servers. A client and server are generally remote from each other and typically interact through a network, such as the described one. The relationship of client and server arises by virtue of computer programs running on the respective computers and having a client-server relationship to each other.

A number of implementations have been described. Other implementations are in the following claims.

What is claimed is:

1. A system, comprising:
an optical imaging assembly configured to image a sample at an object plane to an image plane;
an image sensor arranged at the image plane and configured to capture images of the sample for a field of view of the system;
a light source configured to emit UV light having a wavelength, $\lambda$;
a spatial light modulator (SLM) arranged to receive the UV light emitted from the light source and to provide a spatially modulated light pattern;
one or more optical elements arranged to receive the spatially modulated light pattern from the SLM and to direct the spatially modulated light pattern to the object plane; and
an electronic controller in communication with the image sensor and the spatial light modulator, the electronic controller being programmed to identify one or more targets in the field of view of the optical imaging assembly and to control the spatial light modulator to selectively direct light from the light source to the one or more targets identified by the electronic controller, such that the one or more targets receive a dose of the UV light in a range from 2,000 $\mu W \cdot s/cm^2$ and 80,000 $\mu W \cdot s/cm^2$.

2. The system of claim 1, wherein the optical imaging assembly is an optical microscope comprising an objective lens and a stage operable to position the sample at the object plane.

3. The system of claim 2, wherein the optical microscope is a confocal microscope.

4. The system of claim 1, wherein the image sensor is a CCD sensor, or a CMOS sensor capable of imaging visible light.

5. The system of claim 1, wherein the wavelength is in a range from 100 nm to 400 nm.

6. The system of claim 1, wherein the spatial light modulator is a microelectromechanical systems (MEMS) mirror, a liquid crystal microdisplay, or one or more galvanometer optical scanners.

7. The system of claim 1, wherein the one or more optical elements image the spatial light modulator to the object plane.

8. The system of claim 7, wherein the one or more optical elements comprise a beam expander.

9. The system of claim 8, wherein the one or more optical elements comprise an objective lens separate from the optical imaging assembly.

10. The system of claim 1, wherein the electronic controller is programmed to identify a first population of biological organisms within a plurality of biological organisms as the one or more targets.

11. The system of claim 10, wherein the light source is configured to emit light having the wavelength, $\lambda$, sufficient to deactivate the first population of biological organisms the electronic controller is programmed to identify.

12. The system of claim 1, wherein the electronic controller is programmed to control the spatial light modulator to selectively direct light from the light source to the one or more targets identified by the electronic controller while the one or more targets are in the field of view of the system.

13. A method, comprising:
    capturing one or more images of a sample using an optical microscope;
    identifying, using an electronic processing system, one or more targets in the sample based on the one or more images; and
    while capturing the one or more images, selectively directing, using a spatial light modulator, UV light having a wavelength $\lambda$ to the one or more targets in the sample based on the identifying, such that the one or more targets receive a dose of the UV light in a range from 2,000 $\mu W \cdot s/cm^2$ and 80,000 $\mu W \cdot s/cm^2$.

14. The method of claim 13, wherein the one or more targets comprises one or more bacterial or eukaryotic cells.

15. The method of claim 13, wherein the one or more targets comprises a fluorescent reporter molecule.

16. The method of claim 13, wherein the spatial light modulator is a microelectromechanical systems (MEMS) mirror, a liquid crystal microdisplay, or one or more galvanometer optical scanners.

17. The method of claim 13, wherein the wavelength is in a range from 100 nm to 1400 nm.

18. The method of claim 13, wherein the wavelength is in a range from 100 nm to 400 nm.

* * * * *